United States Patent [19]

Aebischer et al.

[11] Patent Number: 5,573,528
[45] Date of Patent: Nov. 12, 1996

[54] IMPLANTING DEVICES FOR THE FOCAL RELEASE OF NEUROINHIBITORY COMPOUNDS

[75] Inventors: Patrick Aebischer, Barrington; Patrick A. Tresco, Wakefield, both of R.I.

[73] Assignee: Brown University Research Foundation, Providence, R.I.

[21] Appl. No.: 461,301

[22] Filed: Jun. 5, 1995

Related U.S. Application Data

[60] Division of Ser. No. 912,463, Jul. 13, 1992, which is a continuation-in-part of Ser. No. 369,296, Jun. 21, 1989, abandoned, which is a continuation-in-part of Ser. No. 121,626, Nov. 17, 1987, Pat. No. 4,892,538.

[51] Int. Cl.⁶ .................................................. A61K 9/22
[52] U.S. Cl. .................... 604/891.1; 128/898; 128/899; 424/424
[58] Field of Search ........................ 604/890.1, 891.1, 604/27, 28, 93, 36, 43, 116; 623/11, 12; 424/422–424; 128/897–899; 435/180, 182, 41

[56] References Cited

U.S. PATENT DOCUMENTS

| | | | |
|---|---|---|---|
| 4,883,666 | 11/1989 | Sabel et al. | 424/422 |
| 5,182,111 | 1/1993 | Aebischer et al. | 424/424 |
| 5,360,610 | 11/1994 | Tice et al. | 424/426 |
| 5,403,861 | 4/1995 | Goldin et al. | 514/634 |

OTHER PUBLICATIONS

Winn et al, "An Encapsulated Dopamine–Releasing Polymer Alleviates Experimental Parkinsonism in Rats", *Experimental Neurology*, 105, pp. 244–250 (1989).

Primary Examiner—Randall L. Green
Assistant Examiner—V. Alexander
Attorney, Agent, or Firm—Flehr, Hohbach, Test Albritton & Herbert

[57] ABSTRACT

Methods are disclosed for the alleviation of movement disorders via the implantation of static devices which focally release neuroinhibitory compounds to preselected brain areas. Pathological conditions to be treated by these methods include parkinsonian movement disorders, Huntington's chorea, and epileptiform seizure activity. In the treatment of parkinsonism, target areas implantation include the subthalamic nucleus, the globus pallidus internus, and the substantia nigra pars reticulata. In the treatment of epilepsy, implants may be placed in an epileptogenic focus area of neural over-activity. The devices may be polymeric implants that release neuroinhibitory compounds such as GABA, GABA agonists, GABA potentiators, action potential blockers and voltage dependent calcium channel blockers, and glutamate antagonists. Alternatively, the devices may contain living cells which secrete neuroinhibitory compounds.

19 Claims, 3 Drawing Sheets

IMPLANTING DEVICES FOR THE FOCAL RELEASE OF NEUROINHIBITORY COMPOUNDS

CROSS-REFERENCE TO RELATED APPLICATION

This application is a division application of U.S. patent application Ser. No. 07/912,463, filed Jul. 13, 1992, now pending which is a continuation-in-part application of U.S. patent application Ser. No. 07/369,296, filed Jun. 21, 1989, now abandoned, which is a continuation-in-part application of U.S. patent application Ser. No. 07/121,626, filed Nov. 17, 1987, now U.S. Pat. No. 4,892,538.

BACKGROUND OF THE INVENTION

The technical field of this invention is the treatment of movement disorders by implanting in preselected brain sites devices which focally release neuroinhibitory compounds. Candidate movement disorders for this treatment include Parkinson's disease, Huntington's chorea, and epilepsy.

Neuroinhibitory compounds include the inhibitory neurotransmitters gamma amino-butyric acid (GABA) and in some cases dopamine. Neurotransmitters are small molecules (less than 1 kilodalton (kD) molecular weight) which act as chemical means of communication between neurons. They are synthesized by the presynaptic neuron and released into the synaptic space where they then act on receptors specific for that particular neurotransmitter on postsynaptic neurons. GABA is considered a general inhibitory neurotransmitter, since receptors for GABA have been identified in every brain region studied to date (Krnjevic, K., 1991, IN: *GABA Mechanisms in Epilepsy*, Wiley-Liss, pp. 47–87).

Paralysis agitans, more commonly known as Parkinson's disease, is characterized by a lack of the neurotransmitter, dopamine, within the striatum of the brain, secondary to the destruction of the dopamine secreting cells of the substantia nigra. The loss of these dopamine secreting cells disrupts the normal activity pattern of certain neural pathways through the basal ganglia to the thalamus. It is postulated that one result of these alterations in basal ganglia activity is an increase in the activity of certain neurons inhibitory to the thalamus, thereby decreasing excitatory stimulus from the thalamus to the motor cortex. For normal movement, excitatory thalamic signals are required to modulate signals from the motor cortex to the muscles of the body. Subjects with parkinsonian symptoms display movement disorders including stiffness and slowness of movement and rhythmic tremor of limbs.

These clinical symptoms can be improved by the systemic administration of dopamine precursors such as levodopa (L-dopa) (Calne et al. (1969) *Lancet* ii:973–976), or dopamine agonists such as bromocriptine (Caine et al. (1974) *Bri. Med. 3.* 9:442–444) and (+)-4-propyl-9-hydroxynapthoxacine (de Yebenes et al. (1987) *Movement Disorders* 2:291–299), all of which are able to cross the blood-brain barrier. Dopamine, itself, cannot be administered systemically because of its inability to cross the blood-brain barrier. It has been discovered and disclosed in U.S. Pat. No. 4,892,538 that localized delivery of dopamine to the striatum can alleviate certain parkinsonian movement disorders.

As an adjunct or alternative to dopamine therapy, treatment with the inhibitory neurotransmitter GABA has been considered. Postmortem brain studies have shown that patients with Parkinson's disease have decreased basal ganglia GABA function in addition to dopamine deficiencies (Bennet, J. P., et al., 1987 *Ann. Neurol.* 21:41–45). Using experimental animal models for Parkinson's, GABA and its agonists have been administered through systemic or intraventricular routes, or by acute localized infusion to the basal ganglia (Bennet, J. P. et al. supra; Saji, M., et al. 1987 *Science* 235;66–69; Carvey, P. M. et al. 1991 *Movement Disorders* 6:272). As with similar types of dopamine therapy, the systemic or intraventricular application of GABA in human patients would likely lead to undesirable side effects because the inhibitory neurotransmitter would also affect GABA receptors in brain areas unrelated to the pathological condition. Localized infusion through cannulae of GABA-mimetic drugs would be inconvenient and would likely be associated with problems such as infection and mechanical failure of pumping devices.

Stereotaxic surgery, or the placement of precisely localized lesions in the brain has been practiced in some patients, and this procedure appears to provide some relief of parkinsonian symptoms in certain cases. The procedure is risky, however, and opinions among neurosurgeons differ as to the best way of making the lesion and what its ideal location should be. Lesions in various regions of the basal ganglia, for instance in the sub-thalamic nucleus (STN) and in the globus pallidus internus (GPi), have been tried with various levels of success in alleviating parkinsonian movement disorders. These locations (STN and GPi) were chosen for destruction based on the hypothesis that, in parkinsonian disorders, excessive activity (disinhibition) of neurons with cell bodies located in the STN and/or the GPi (see FIG. 1) leads to abnormal inhibition of thalamic neurons. The excitatory activity of thalamic projections to the motor cortex is required for normal movement. Thus, it was postulated that the success of lesions to the STN and the GPi was due to interruption of pathways leading to excessive inhibition of thalamic neurons. (For a review of this hypothesis, see Aebischer, P., et al., 1991, *Science* 252:133.) Lesioning of specific brain areas as therapy is problematic, however, because the lesion necessarily destroys all neurons in the selected area, including those that are functioning normally. Huntington's chorea is a genetically transmitted disease characterized by the onset in middle age of choreiform movement disorders. One affected brain area in Huntington's disease, like Parkinson's disease, is thought to be the basal ganglia. In contrast to Parkinson's, however, the dopaminergic neurons of the substantia nigra are thought to be intact in Huntington's disease. In Huntington's, there is a generalized destruction of neurons having cell bodies in the striatum. This degeneration affects the output of the striatum to the GPe, the GPi and the SNpr, among others. Similar to Parkinson's disease, loss of striatal efferent connections to these nuclei results in a generalized disinhibition of the GPi and SNpr thalamic outputs. Treatment has generally been limited to tranquilizers, phenothiazines, and other drugs which act systemically and non-specifically to depress the central nervous system. It has been shown in a number of animal models that treatment with GABA can lead to amelioration diskenisia.

There exists a need for methods to correct malfunctioning pathways of the basal ganglia without causing excessive trauma. More specifically, there exists a need for methods to specifically inhibit the activity of neurons within preselected brain nuclei of the basal ganglia in order to alleviate movement disorders associated with Parkinson's and Huntington's diseases.

Epileptic seizures represent another form of movement disorder associated with neuronal over-activity. In contrast to Parkinson's disease and Huntington's chorea, however, the area of epileptic neuronal over-activity may be unique to each individual sufferer.

Seizures may originate in a temporal lobe, in other limbic structures, or in cortical areas that project to limbic areas, including frontal and occipital cortex. Over-activity in basal ganglia, thalamic, and brainstem nuclei accompanies some clinical signs of focal seizure activity. Spread of over-activity often involves certain common structures such as the parahippocampal cortex, hippocampus, and amygdala. (Meldrum, B. S., 1990, The Lancet 336:231–234).

Standard treatment for epilepsy currently involves the chronic systemic administration of drugs which act as general central nervous system depressants, often with accompanying side-effects such as sedation and allergic reaction (Brodie, M. J., et al., 1990, The Lancet 336:425–426; Porter, R. J., 1990, The Lancet 336:423–424). Drug treatment for epilepsy during pregnancy and lactation presents special problems such as teratogenesis (three times the background rate) and neonatal sedation (Brodie, M. J., 1990, The Lancet 336:426–427).

An electrical implant ("neurocybernetic prosthesis") has been proposed as a method to prevent seizures by electrically interfering with neuronal signals (Lehrer, N. E., WO 85/01213, Mar. 28, 1985).

In severe cases, when seizures cannot be controlled by drugs, surgical removal of parts of the limbic system can sometimes break the neural circuit within which seizure activity becomes established, thereby decreasing seizure activity (Meldrum, B. S., supra). Clearly, removal of part of the brain is a treatment of last choice. What is needed is a method for the inhibition of neuronal over-activity in a specific epileptogenic area which would allow a neuroinhibitory drug to reach the desired area in an effective concentration, without causing undesirable side-effects.

SUMMARY OF THE INVENTION AND OBJECTS

Methods are disclosed for decreasing abnormal over-activity in a neural pathway by implanting a static device which focally releases a neuroinhibitory compound to target neurons; the compound inhibits over-activity in the target neurons and thereby decreases over-activity in the neural pathway in which the target neuron is synaptically connected.

One embodiment of the invention is directed to the alleviation of movement disorders associated with Parkinson's and Huntington's diseases through implantation of devices in brain nuclei of the basal ganglia, which includes the subthalamic nucleus (STN), the globus pallidus internus (GPi), the substantia nigra pars reticulata (SNpr), substantia nigra pars compacta (SNpc), ventrolateral thalamic nucleus (VLTN), and the striatum.

A second embodiment of the invention is directed to the alleviation of epileptiform seizures through implantation of devices which release neuroinhibitory compounds to foci of epileptogenic neural over-activity.

The invention is further directed to the focal implantation of devices which release neuroinhibitory compounds such as GABA, GABA agonists, GABA potentiators, action potential blockers, voltage dependent calcium channel blockers, glutamate antagonists, phenytoin, carbamezepine, valproate, barbiturates, benzodiazepines, ethosuximide, tetrodotoxin, saxitoxin, and conotoxins.

BRIEF DESCRIPTION OF THE DRAWINGS

FIG. 1 shows certain neural pathways through the basal ganglia to the thalamus and cortex. These neural pathways are the major pathways involved in parkinsonian movement disorders and in Huntington's chorea. 1 substantia nigra pars compacta (SNpc), 2 substantia nigra pars reticulata (SNpr), 3 striatum, 4 globus pallidus externus (GPe), 5 sub-thalamic nucleus (STN), 6 globus pallidus internus (GPi), 7 thalamus, 8 motor cortex. The black arrowheads represent neuronal terminals of axons which originate in the brain nucleii from which the arrows project.

Neuronal connectivity is indicated by interconnecting arrows. The arrows indicate neuronal projections originating in the nucleus from which the arrow projects and the black arrowheads indicate the location of the synaptic terminals of the neuronal pathways.

The neuronal terminals of axons "a" release dopamine in a normal individual. This dopamine binds to either the D1 (inhibitory) or D2 (excitatory) dopamine receptors present in the striatum. For all synapses diagrammed, "+" or "−" indicates whether transmitter release has an inhibitory or activating effect on the post synaptic neuron of the synapse. Except for the dopaminergic synapses of the striatum, the neurotransmitter released at a particular synapse is also indicated on the diagram. "GABA" refers to γ-aminobutyric acid and "GLUT" to glutamate.

DETAILED DESCRIPTION OF THE INVENTION

The term "static device" refers to a device (suitably of the type disclosed in U.S. Pat. No. 4,892,538) which contains and releases neuroinhibitory compounds when implanted in selected brain areas for chronic delivery during long-term implantation. The term excludes the use of internal or external pumps used in conjunction with the static device to drive the compounds from a reservoir to the selected brain areas. Thus, the form of the static device may include an implantable polymeric insert, a device having a semipermeable wall for releasing such compounds from secretory cells, or other implantable containers for such compounds.

When implanted in the selected brain areas, the static devices release neuroinhibitory compounds in order to ultimately effect the normalization of neural signals from the motor cortex to the muscles of the body. It is generally believed that for normal movement of the muscles, motor cortex signals are modulated by excitatory signals from the thalamus (Filion, M., et al., 1991, Brain Research 547:142–151). In Parkinson's disease and in Huntington's disease, thalamic signals to the motor cortex are believed to be abnormally inhibited.

The term "parkinsonian movement disorders" refers to a collection of symptoms such as stiffness and slowness of movement. The parkinsonian movement disorders may be caused by Parkinson's disease, secondary to the destruction of dopamine-secreting cells of the substantia nigra. Parkinsonian movement disorders may also be caused by repeated trauma to the head as seen in certain athletes, most notably boxers. Parkinsonian movement disorders were also identified in drug addicts who had used a form of synthetic heroin which destroyed cells of the substantia nigra (Burns, R. S., et al., PNAS 80:4546–4550, 1983). Parkinsonian movement disorders may be induced experimentally in laboratory animals by the injection of 6-hydroxydopamine into the substantia nigra (Winn, S. R., et al., *Experimental Neurology* 105:244–250, 1989) or by the intravenous injection of N-methyl-4-phenyl-1,2,3,6-tetrahydropyridine (MPTP) (Burns, R. S. et al., supra; Robertson, R. G., et al., *Brain Research* 563:278–280, 1991; Filion, M., et al., supra).

Figure 1:
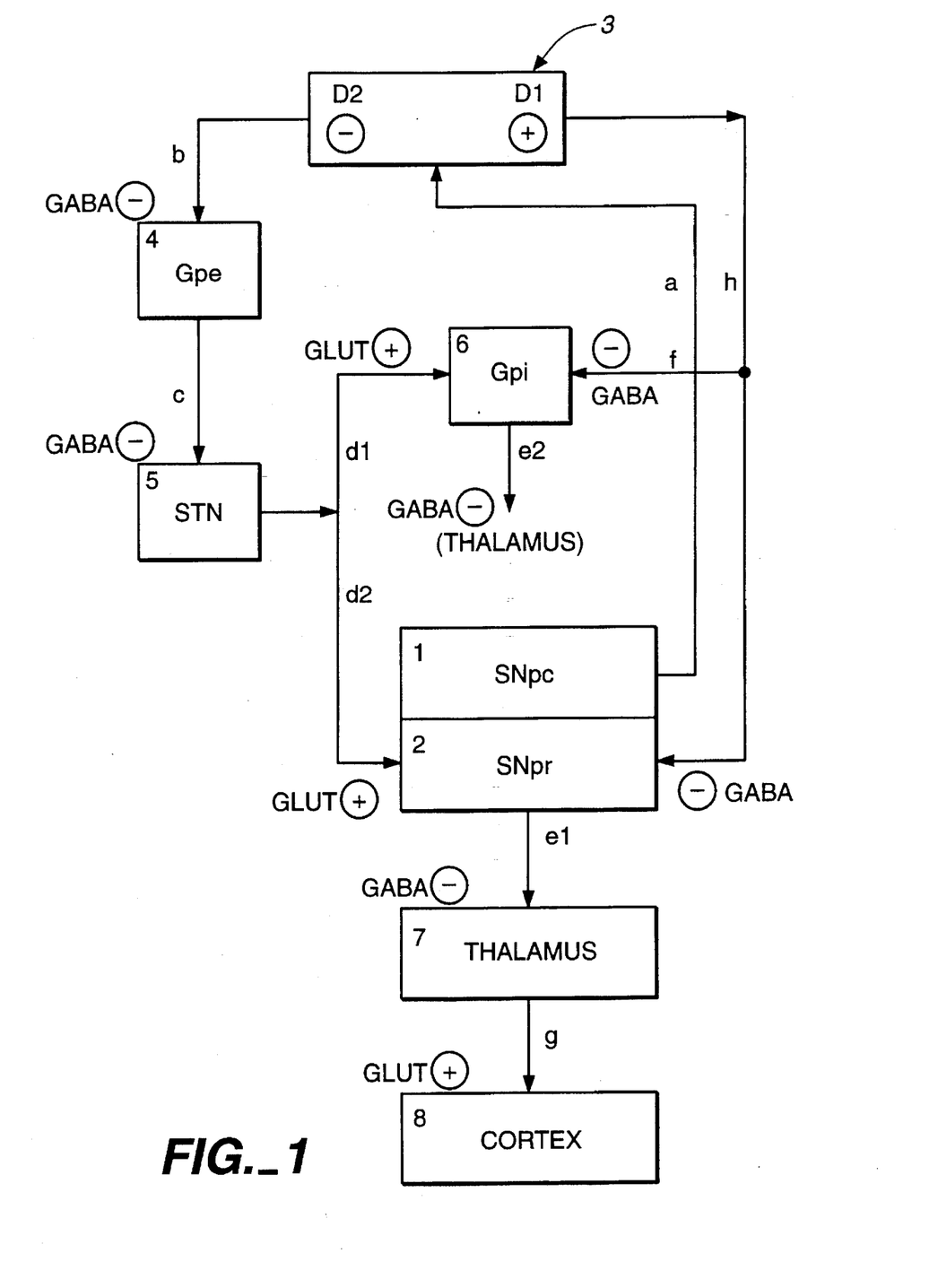

FIG. 1 depicts major neural pathways through the basal ganglia to the thalamus and to the cerebral cortex. In FIG. 1, numbers (1–8) designate major brain areas, known as "nuclei" which contain neuronal cell bodies. From these cell bodies, neuronal axons project to other nuclei. Neuronal axons are designated with letters ("a" through "g"). It is believed that, in the brain of an individual without movement disorders, the neural transmission is as follows. Neurons with cell bodies in the substantia nigra pars compacta (SNpc, 1) have axons (a) which project to the striatum (3) where they tonically release dopamine at synapses with certain cell bodies located in the striatum (3). Dopamine inhibits the firing of striatal neurons having D2 inhibitory dopamine receptors (axons "b"). Dopamine excites striatal neurons having D1 excitatory dopamine receptors (axons "h"). Striatal D1 receptor containing neurons have axons "h" which project to the globus pallidus internus (GPi, 6) and the substantia nigra pars reticulata (SNpr, 2). Axons "h" release GABA from synapses with cells in these nucleii. Neurons in both of these nucleii also receive stimulatory input from the sub thalamic nuclei (STN, 5). In the normal state, however, the STN receives tonic inhibitory input and the activity of the excitatory projections to the GPi and SNpr is reduced. Thus, the thalamic outputs from the GPi and the SNpr under normal conditions, are largely inhibited. Striatal D2 receptor containing neurons have axons ("b") which project to the globus pallidus externus (GPe, 4). Axons "b" release GABA at synapses with neurons of the GPe(4). However, since normally the firing of "b" is tonically inhibited by dopamine, the net effect on the firing of the neurons in the GPe(4) is positive, i.e. neurons in the GPe are allowed to be normally active. Neurons in the GPe have axons, "c", which project to the sub-thalamic nucleus (5), where they tonically release GABA at synapses with neurons of the sub-thalamic nucleus (5). Since GABA is an inhibitory neurotransmitter, the net effect on the firing of neurons of the sub-thalamic nucleus (5) is negative, i.e. neurons of the sub-thalamic nucleus are inhibited in their firing. Neurons of the subthalamic nucleus (5) have axons "d1" which project to the globus pallidus internus (GPi, 6), where they release glutamate at synapses with neurons of the GPi (6). Glutamate is an excitatory neurotransmitter; however, since axons "d1" are normally inhibited in their firing, there is little or no net excitatory effect on neurons of the GPi(6). Neurons of GPi(6) have axons "e2" which project to the thalamus (7) and release the inhibitory neurotransmitter GABA at synapses with neurons in the thalamus. However, since the firing of axons "e2" is not stimulated by the action of "d1", and axons "e2" receive inhibitory input from the striatum via axons "f" there is little or no net inhibitory effect on the firing of neurons of the thalamus (7). Excited neurons of the thalamus (7) then project axons "g" to the cortex where they release the excitatory neurotransmitter, glutamate. Normally, then, the net effect of thalamic axonal projections "e2" via "g" to the cortex is excitatory. Another ultimately excitatory loop to the cortex, similar the "d1"—"e2"—"g" loop, is thought to run from the subthalamic nucleus(5) via axons "d2" to the substantia nigra pars reticulata (SNpr,. 2). In the SNpr, the diminished excitatory input from axons "d2" is further complemented by increased inhibitory input from axon "h" arising in the striatum. SNpr output continues then via axons "e1" to the thalamus (7) and via axons "g" to the cortex. It is believed that these excitatory projections from the thalamus to the cortex are necessary for normal movement.

It is generally believed that certain parkinsonian movement disorders as well as Huntington's chorea can be traced to abnormal inhibition of the above described thalamic neurons which project to the cortex (FIG. 1, "g"). In Parkinson's disease, this thalamic neuron inhibition originates with the destruction of dopaminergic input to the striatum (FIG. 1 "a"). The destruction of inhibitory dopamine releasing neurons leads to serial changes in neural signals along the above described pathways in the basal ganglia leading to the thalamus, and ultimately to the cortex. It is believed that, when dopamine releasing synapses degenerate in the striatum (3), the net neuronal activity within the above described loops are reversed from normal. At certain points in these pathways, there may be over-active inhibitory signals, or over-active excitatory signals. For example, in Parkinson's disease, the relative firing patterns of axons projection from the striatum is reversed. Thus, those neurons containing D2 receptors are no longer tonically inhibited, while those containing D1 receptors and projecting to the GPi and Snpr are no longer activated in the normal pattern. (Note that the activity of axon "f" would tend to be diminished due to lack of striatal excitation. The normal inhibitory input provided by axons "f" would then be missing, further augmenting the firing of the inhibitory e2 axons. A similar situation exists for the SNpr.) Thus, net activity at the GPi(4) inhibitory, at the subthalamic nucleus(S) excitatory, at the GPi(6) excitatory, at the SNpr(2) excitatory, at the thalamus (7) inhibitory. Thus, the normal excitation of thalamic neurons "g" which project to the cortex (8) are abnormally inhibited, and contribute to the abnormal movement disorders of Parkinson's disease. (Filion, M., et al., supra; Aebischer, P., et al., supra.)

In the case of Huntington's disease, there is destruction of a number of neuronal types within the striatum, including neurons which project to the GPi, the GPe and the SNpr. This tends to leave these nucleii relatively "under-inhibited" and therefore effects on thalamic output similar to Parkinson's disease may occur. Thus, the preferred targets for inhibition of abnormal neuronal activity occurring in Huntington's disease include the GPe, the GPi and the SNpr. Inhibition of combinations of the three targets would probably have optimal effects.

In order to disrupt abnormally active pathways of the basal ganglia, static devices which release neuro-inhibitor compounds may be implanted adjacent one or several of the above named target nuclei to provide focal release of the compound to the nuclei. (The term "adjacent" means that the device is close enough to the target nuclei that the released compounds contact the target nucleii.) Inhibition of the activity of target neurons within these nuclei by neuroinhibitory compounds causes changes in activity throughout the neural pathways leading to the thalamus (see FIG. 1). These changes, in turn, restore thalamic excitatory output to the motor cortex (FIG. 1 "g"). The use of this invention allows the neuroinhibitory compound to be released for prolonged periods of time, to a circumscribed, preselected area of the brain with the need for external connection, which reduces the risk of side affect and infection.

In Parkinson's disease, the STN, the GPi, and the SNpr. contain over-active neurons which may be inhibited by neuroinhibitory compounds released from an implanted device.

Herein, the term "activity" refers to neural activity characterized by a series of action potentials being propagated along the neuronal axon to the synaptic ending, resulting in the release of a neurotransmitter at the synapse. When the released neurotransmitter is inhibitory in nature (e.g. GABA), it acts on the next neuron in the pathway to inhibit the propagation of action potentials along its axon, and ultimately to inhibit the release of neurotransmitter from that neuron at the next synapse in the pathway. Conversely, when the released neurotransmitter is stimulatory in nature (e.g. glutamate) it acts on the next neuron in the pathway to stimulate the propagation of action potentials and to stimulate the release of neurotransmitter from that neuron at the next synapse in the pathway.

Herein, the term "over-active" refers to a higher than normal action potential firing rate and/or the release of abnormally large amounts of neurotransmitter, over time, at the synaptic terminal of the neuron in question. The transmitter may be either inhibitory or excitatory in its action, depending on the nature of the over-active neuron.

For example, in Parkinson's disease, the sub-thalamic nucleus (FIG. 1, 5) contains projections from abnormally inhibited neurons (FIG. I, "c") which would normally release sufficient amounts of the inhibitory neurotransmitter GABA to inhibit the activity of axons "d2". Since axons "d2" are now released from GABA inhibition, they are over-active; they release an abnormally large amount of the excitating neurotransmitter, glutamate, which in turn causes axons "e1" to be over-active and to release abnormally large amounts of the inhibitory neurotransmitter, GABA, to the thalamus. These effects are complemented by the lack of excitation of GABA releasing neurons "f". In order to decrease the abnormal over-activity of axons "e1", a device which releases a neuroinhibitory compound may be implanted at or near the subthalamic nucleus to decrease the over-activity of axon "d2".

Herein, the term "target neuron" refers to any neuron such as those within the loops described in FIG. 1, any part or all of, to which the neuroinhibitory compound is directed.

In the above example, the target neurons are "d2", which may be in direct synaptic connection with the "output neurons", "e1".

Herein, the term "output neuron" refers to any neuron within the loops such as those described in FIG. 1 which receives innervation, either directly or indirectly, from a target neuron, the target neuron being overactive.

Herein, the term "direct synaptic connection" refers to the transmission of neural signal from one neuronal terminal, across the synaptic junction, to the cell body or dendrites of the next neuron in the pathway.

There may exist "interneurons" between the target neuron and the post-synaptic output neuron. Herein, the term "interneuron" is defined as a neuron which receives a neural signal from the target neuron and transmits the neural signal to a post-synaptic neuron. The interneuron's signal transmittal may be via its direct synaptic connection with the output neuron, or it may be via transmittal through one or more interneurons.

Herein, the term "positioned pre-synaptically" refers to a target neuron's position "upstream" within a pathway so that an effect on the target neuron will ultimately be transmitted via one or more synapses to the output neuron.

The present invention is directed to action on a target neuron which receives functional synaptic input. Herein, the term "functional synaptic input" refers to the normal contact of an axonal terminal with a synapse on the axon, cell body and or dendrites of the target neuron, and the release of the normal type of neuro-transmitter at that synapse. Thus, for example, when neurons "b" are deprived of input from dopaminergic neurons "a" as described in U. S. Pat. No. 4,892,538, neurons "b" are considered to be deprived of "functional synaptic input" and are not considered as target neuron in this invention. In contrast, where neurons of the striatum or of any part of the basal ganglia receive signals via a neurotransmitter released by a neuronal terminal at a synapse, these neurons may be considered as target neurons in the present invention for the treatment of movement disorders due to Parkinson's or Huntington's disease.

In the case of Huntington's disease, there is destruction of a number of neuronal types within the striatum, including neurons which project to the GPi, the GPe and the SNpr. Thus, the preferred targets for inhibition of abnormal neuronal activity occurring in Huntington's disease would include the GPe, the GPi and the SNpr. Inhibition of combinations of the three targets would tend to have optimal effects.

In practicing this invention for the treatment of Parkinson's disease, another preferred site for implantation is in or near the GPi (FIG. 1,6), which is relatively conveniently located in the brain for stereotaxic placement of the device. The neuro-inhibitory compound released by the device located in the GPi decreases abnormal over-activity of inhibitory neurons (e2) of the GPi which project directly to the thalamus. When the activity of these inhibitory neurons is decreased, the normal excitatory signals from the thalamus to the motor cortex are restored, leading to alleviation of movement disorders.

Figure 2:
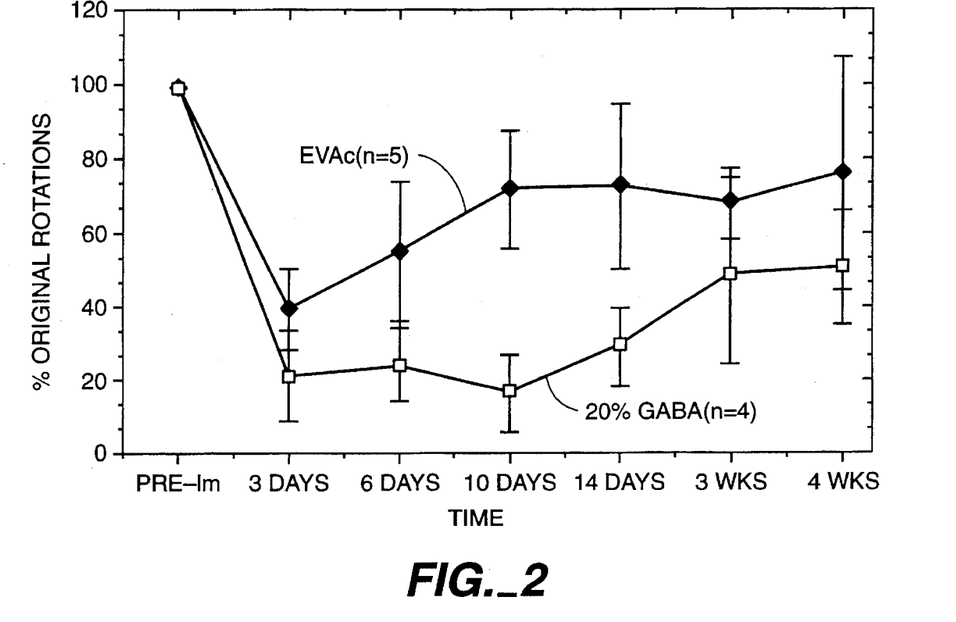
FIG. 2 is a graphic depiction of the changes in rotational behavior of rats bearing 6-OHDA lesions, an experimental model for parkinsonian movement disorders. Rats were implanted with devices which released GABA (hollow squares) or control devices (solid circles).

As illustrated in FIG. 1, another preferred implantation site is the SNpr (FIGS. 1, 2). As described above, neurons which project from the PRsn to the thalamus (e1) are believed to be abnormally active (i.e., inhibitory to the thalamus) in Parkinson's disease. A neuroinhibitory compound released from a device located in the PRsn inhibits the inhibitory signals from the PRsn to the thalamus, restoring excitatory signals from the thalamus to the motor cortex.

Other effective sites for implantation of devices which release neuroinhibitory compounds in order to alleviate movement disorders arising from over-activity within the basal ganglia would be apparent to those skilled in neurology and neurosurgery.

Another embodiment of the present invention is directed to the alleviation of seizure activity due to epilepsy. In contrast to movement disorders due to Parkinson's or Huntington's disease, in which the over-active pathways are thought to be in the basal ganglia, epileptic seizure activity may originate with neural over-activity in varying brain regions, depending on the individual patient. For a given patient, the epileptogenic focus of neural over-activity remains constant. Herein, the term "focus" refers to the original area of neural over-activity, which then spreads via various pathways to result in over-activity within the motor cortex. Herein, the term "epileptogenic area" refers to any area of neural over-activity, including both the original focus area and areas to which the over-activity has spread (Meldrum, B. S., supra).

In practicing the present invention, an epileptogenic area or the focus area is identified for each individual patient. This area may then be selected as a target area for implantation of a device which releases a neuroinhibitory compound. Epileptogenic areas may be identified by means of several diagnostic techniques including EEG (electroencephalography), CT (computerized tomography), NMR (nuclear magnetic resonance), SPECT (single photon emission computed tomography) or PET (positron emission tomography). Devices may then be implanted at or near the appropriate epileptogenic area by means of imaging combined with stereotaxic surgery. The device is engineered so that a minimum dose of the neuro-inhibitory compound is released sufficient to alleviate the seizure activity without appreciable side-effects.

Animal models for epilepsy are available for preclinical testing of treatments for epilepsy (Sperber, E. F., et al., 1987, *Developmental Brain Research* 37:243–250). GEPr mice respond to sound and light stimuli with seizure activity. The appropriate implantation of a device which releases a neuroinhibitory compound delays the onset and reduces the severity of this seizure activity.

We turn now to the types of compounds which are useful in practicing the invention. Herein, the term "neuro-inhibitory compound" refers to any substance which, when applied to the neuronal cell body, to the dendrites, or directly to the axon, is capable of decreasing neurotransmitter receptor activation of one or more neurons directly post-synaptic to the target neuron. The mechanism by which the compound decreases post-synaptic receptor activation will most often involve a decrease in transmitter release by the target neuron. In most cases, this will involve a reduction of action potential generation in spiking target neurons, or a net hyperpolarization or decrease in membrane resistance in non-spiking interneurons. However, other means of reducing transmitter release such as reduction of quantal size, or frequency may also be useful. Thus, drugs such as verapamil which decrease synaptic calcium influx are potentially useful.

It is preferred, but not required, that the effect of the compound is reversible and does not result in cell death. In most cases, the compound will generally inhibit or diminish all neuronal activity in the immediate target region, but as it diffuses away, its concentration will decrease so that neurons farther removed from the target will be unaffected. As a general rule, devices which release compounds which act via a specific receptor are designed to generate local concentrations of the compound of approximately 2 times the binding affinity (kD) of the compound for its receptor. Information on the binding affinities of most compounds is readily available in the published literature. The devices may be tested in vitro for their release characteristics prior to implanting in an individual.

Particularly advantageous neuroinhibitory compounds are the neurotransmitter GABA and its agonists, because virtually all neurons of the central nervous system are subject to inhibition by GABA. Inhibition by GABA occurs through its specific action on neuronal GABA receptors which, when contacted by GABA, alters neuronal excitability. Also useful are potentiators of GABA release and inhibitors of GABA reuptake, although they are more effective in those areas where GABA is already being released by neurons at or near the target area.

Examples of GABA-mimetic drugs include the GABA agonist muscimol, certain specific pyridine derivatives (EP 338, date=790124), and isonicotinic acid derivatives (U.S. Pat. No: 4,301,287, date=811117). GABA prodrugs such as progabide and gamma-vinyl GABA neurosteroids may also be useful. Piperidine derivatives with GABA-uptake-inhibiting activity may be used (U.S. Pat. No: 4,910,312, date= 900320) as well as GABA transaminase inhibitors such as gabaculine, and 5-amino 1,3-cyclohexadiene-1-carboxylic acid (U.S. Pat. No: 4,187,316, date=800205).

Compounds which disrupt signaling in other ways are also useful in practicing this invention. Such compounds may act by 1) generally decreasing transmitter release from the target neurons; 2) generally decreasing the excitability of the target neurons; or 3) blocking the response of a post-synaptic neuron to a neurotransmitter. It is likely that many compounds exert their inhibitory actions through more than one of the above mechanisms.

Certain drugs known to be useful for the control of epilepsy via systemic delivery may be used for focal delivery in the present invention for the treatment of Parkinson's and Huntington's disease as well as epilepsy. These drugs, which include phenytoin, carbamezepine, valproate, barbiturates, and benzodiazapines, are believed to effect neuroinhibition via more than one membrane-mediated mechanism (Rogawski, M. A., et al., 1990, *Pharmacological Review* 42:223–286; Brodie, M. J., et al., supra).

Examples of substances which generally decrease transmitter release include compounds which decrease intracellular calcium levels, particularly those compounds known to be blockers of calcium channels.

Ethosuximide is known to specifically decrease calcium flux through the T-channels, which are not widely distributed within the central nervous system, but which are known to be present on neurons within the thalamus. The thalamus is currently believed to be a common epileptogenic area, and ethosuximide is known to alleviate generalized seizure activity in many epileptic patients. Thus it is postulated that ethosuximide achieves its effect via action on the T-channels within the thalamus, and is therefore a preferred compound for focal release to the thalamus in practicing the present invention for the alleviation of generalized epileptic seizures. Other general calcium channel blockers include phenytoin, barbiturates, verapamil, benzodiazapines, and the peptides dynorphin, omega-conotoxin, and omegaagatoxin. These compounds may be used to advantage in the present invention because focal release allows sufficient concentration of a drug to reach the target neurons without the side effects expected from systemic administration of an effective concentration. Also, focal release allows a given drug to reach its target neuron quickly before it is broken down, either enzymatically or by other degradation means.

Neuronal over-activity may also be inhibited by action-potential blockers which act on the sodium channel. Examples of such compounds include phenytoin, valproate, carbamazepine, and other water soluble compounds known to the art.

Another type of neuroinhibitory compound is a substance which specifically inhibits a receptor for an excitatory neurotransmitter. Glutamate antagonists are within this class of neuroinhibitory compound. Thus, a glutamate antagonist is useful for inhibition of a target neuron which is over-active because of excessive stimulation-by glutamate (see for example FIG. 1, "e1"). In addition, glutamate antagonists are often effective even when a neuron is not over-stimulated by glutamate.

The device of the present invention belongs to a broad family of devices, including polymeric implants and cell-containing implants, as described below.

The source of a neuroinhibitory compound, such as GABA, may be incorporated into a polymeric insert as described in U.S. Pat. No. 5,106,627 and as described herein in Example 1. The encapsulating material provides a protective environment for the drug embedded therein, while affording sustained release of the drug at a controlled rate therefrom. For instance, the use of a polymeric insert composed of hydrophobic matrices reduces chemical degradation by inhibiting oxidation and hydrolysis of the drug encapsulated therein.

The concentration of drug added to the matrix material is one factor controlling the rate of drug release; the more drug incorporated, the more rapid the release rate. The particulate amount of the drug incorporated into the matrix material is another variable; the larger the particle size, the quicker the rate of release.

An alternate form of device is one which contains cells which secrete the neuroinhibitory compound. For a detailed description of cell-containing devices, see U.S. Pat. No: 4,892,538, which is herein incorporated by reference. Such implantable devices may take any shape which will accommodate the cells to be encapsulated and which will not cause undue trauma upon surgical implantation. The cells may be contained in a device in the form of a tube composed of a biocompatible, selectively permeable membrane having pores in the range of 50 kD to 1000 kD. The cells may also be contained within alginate microcapsules, as described in U.S. Pat. No. 4,409,331, filed 28-APR-1982. Preferably, the cells are contained in retrievable macrocapsules, as described in co-pending U.S. application Ser. No. 07/692,403.

Cells that are known to contain or secrete GABA include adrenal chromaffin cells (Oset-Gasque, M. J., et al., 1990, *J. Neurosci. Res.* 26:181–187); oviduct cells (Fernandez, I., et al., 1991, *Brain Res. Bull.* 26:821–823); and pancreatic beta cells (Reetz, A., et al., 1991 *EMBO Journal* Volume:1275–1284). Furthermore, we have found that the pancreas derived RIN and NIT beta cell lines secrete GABA (Example 3).

Alternatively, cells may be genetically engineered to express and release a neuroinhibitory peptide. These genetically engineered cells may then be encapsulated in the device of the invention.

Cells which have been genetically engineered to produce GABA may be useful in practicing this invention. Thus, in such an approach, the gene which encodes glutamic acid decarboxylase (GAD: the enzyme Erlander, M. G., et al., 1991 *Neurochemical Res.* 16:215–226, which promotes the synthesis of GABA) is either isolated from a cell line or constructed by DNA manipulation. The gene can then be incorporated int a plasmid, which, in turn, is transfected into a cell such as a fibroblast or a PC12 cell for expression. (See, e.g., Sainbrook et al., Molecular Cloning. A laboratory Manual. (1989), for further discussion of cloning .vehicles and gene manipulation procedures.) Such genetically engineered GABA-producing cells may be encapsulated into the implants destined for appropriate brain areas. The construction of cell-containing implants is described in U.S. Pat. No. 5,106,622.

The static device of the present invention may also contain cells which have been genetically engineered to express and secrete peptide toxins such as omega-conotoxin (Yeager, R. E., et al., 1987 *J. Neuroscience* 7:2390–2396; Adams, M. E., et al., 1990, *J. Biol. Chem.* 265:861–867; Takemura, M., et al.,1989, *Neuroscience* 32:405–416; Yanagawa, Y., et al., 1988, *Biochemistry* 27:6256–6262).

Other peptides such as substance p dynorphin (Gross, R. A., 1990, *PNAS* 87:7025–7029), and "brain derivable polypeptides" (Shoyab, M., et al., WO 86/04239, Jul. 31, 1986) which are known to be neuroinhibitory, may also be expressed and secreted from genetically engineered cells.

Expression of the neuroinhibitory peptide may be designed to be constitutive, resulting in tonic release of the peptide in the target area. In other cases, it may be useful to provide a promoter which can be induced, down-regulated or up-regulated by appropriate stimuli, for example, the "MMTV" hexamethasine-inducible promoter or the "MX" interferon-inducible promoter may be useful. Promoters may also be selected for their ability to be regulated by neural activity, or in response to specific drugs.

The following non-limiting examples more fully illustrate preferred features of the invention.

EXAMPLE 1

GABA-Releasing Implants Alleviate Symptoms in Parkinsonian Model System

Polymeric implants were prepared in similar fashion to the dopamine-releasing implants described in U.S. Pat. No. 5,156,844 (Winn, et al. 1989, *Exp. Neurol.* 105:244–250). Ethylenevinyl acetate copolymer (EVAc) resin (40% by weight vinyl acetate, Elvax 40w, DuPont, Inc., Wilmington, Del.) was washed 20 times in distilled water and 20 times in 95% ethanol to remove impurities. Purified EVAc was subsequently dissolved in methylene chloride to make a 10% (W/v) solution. GABA (Sigma) was ground with a mortar and pestle and then sieved to an average size of 60–70 μm. Particles were then added to the EVAc solution to a final concentration of 10 or 20% (W/W). The GABA/EVAc solution was ultrasonicated for 5 min., agitated in a vortex mixer, and rapidly cooled in liquid nitrogen in order to form a solid matrix with fixed GABA particles. The methylene chloride was removed by lyophilization.

Figure 3:
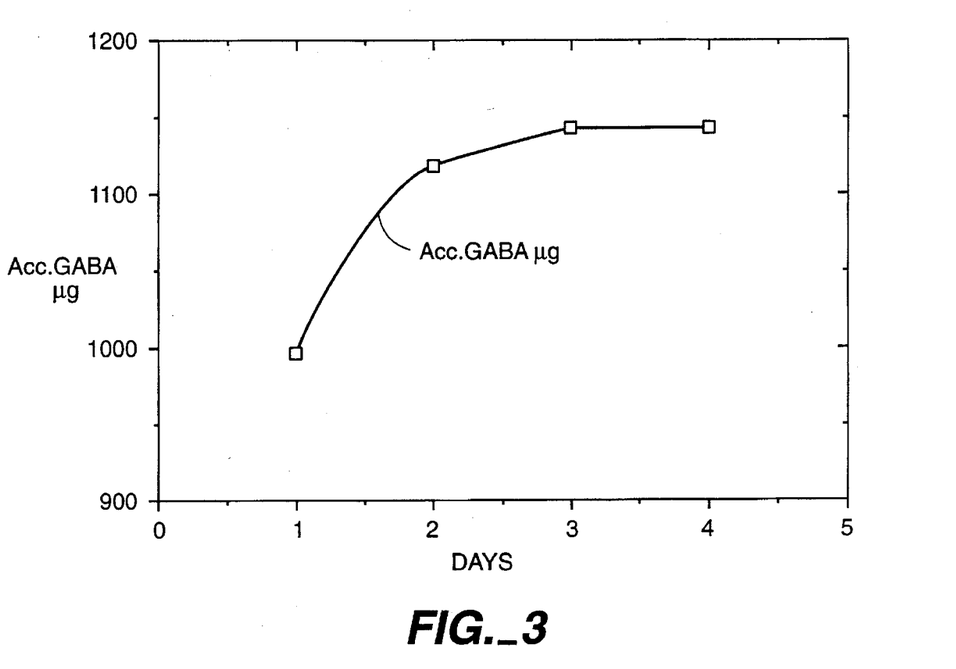
FIG. 3 is a graphic depiction of the sustained release of GABA from polymer rods in vitro. The cumulative release of GABA from an EVAc polymer rod in PBS with a 30% GABA loading is plotted.

Strings with a diameter of 0.5 mm were pressure extruded at a temperature of 55° C. and sectioned into 8 mm long rods. To retard GABA release, three coats of pure polymer were applied to each rod by repeated immersion in 10 % EVAc solution resulting in a final diameter of 0.7 mm. The distribution of GABA particles in the EVAc was analyzed by scanning electron microscopy (AMRay-1000A). Sustained GABA release over four days was determined in vitro (FIG. 3).

Ten Sprague Dawley CD rats were lesioned with 6-hydroxydopamine (6-OHDA) by means of direct injections (10 ug/5 ul) into one side of the substantia nigra according to the method of Winn et al., supra. The success of the lesions in the injected rats was confirmed by testing for apomorphine-induced (0.1 mg/kg) rotational behavior at weekly intervals. (Ungerstedt, U., 1971 Acta Physiol. Scand. suppl. 367:69–93). Apomorphine induces Parkinson's-like motor response of turning away from the side of 6-OHDA induced lesion. The extent of such rotational behavior following apomorphine injection is used initially to monitor the extent of the lesion and then the degree of alleviation provided by the administration of GABA. Six weeks after the induction of Parkinsonian-like symptoms, successfully lesioned animals were anesthetized and placed in a stereotaxic apparatus. The animals received implants to the pars reticulata of either EVAc rods without GABA (controls) or GABA-containing EVAc rods. The stereotactic coordinates used for implantation were: Bregma −5.5, lateral +2, depth −8.5. Following implantation, the animals were tested for rotational behavior at weekly intervals. Prior to implantation, all animals exhibited an equivalent number of rotations after apomorphine administration. Within ten days post-implantation, those animal which received GABA-containing implants exhibited approximately 80% reduction in rotations compared to original rotations (FIG. 2). In contrast, animals which received control implants (without GABA) exhibited only approximately 40% reduction in rotations at ten days post-implant. This indicated that the GABA implants significantly reversed the behavioral effects of the 6-OHDA induced lesions. Histology showed the rods were placed just above the pars reticulata and contained minimal histological reaction to the implants.

EXAMPLE 2

Use of GABA-Releasing Polymeric Implants To Alleviate Experimental Parkinsonian Symptoms in Monkey A single macaca fasicicularis monkey exhibited a contralateral parkinsonian-like movement disorder including bradykinesia, rigid it tremor following a unilateral right side carotid injection of MPTP (Burns, et al., *PNAS* 80:4546 (1983)). The subject was chaired and trained to pick up food rewards from multiwell plates. Bradykinesia was quantified by measuring the time required for each upper limb to independently empty trays loaded with food treats. The animal showed significantly impaired ability to pick food from the tray using the left limb, which was the side affected by the MPTP injection. In order to rule out spontaneous recovery, the time between the MPTP lesions and the capsule implantation was 32 weeks (FIG. 4).

As a control, starting 29 weeks post-lesioning, the animal received oral L-DOPA (100–150 mg/day)/carbidopa (50–75 mg/day) (Sinemet@) twice a day for a period of 10 days. The animal showed no improvement in the picking task performed by the left limb for the duration of the Sinemet treatment (FIG. 4).

Thirty-four weeks post-lesioning, the animal received a single polymeric GABA-releasing implant, which was prepared as described in Example 1, 500 μg dia., 3 inch length. Implants were delivered through a removable cannula positioned stereotaxically to be within the subthalamic nucleus.

Figure 4:
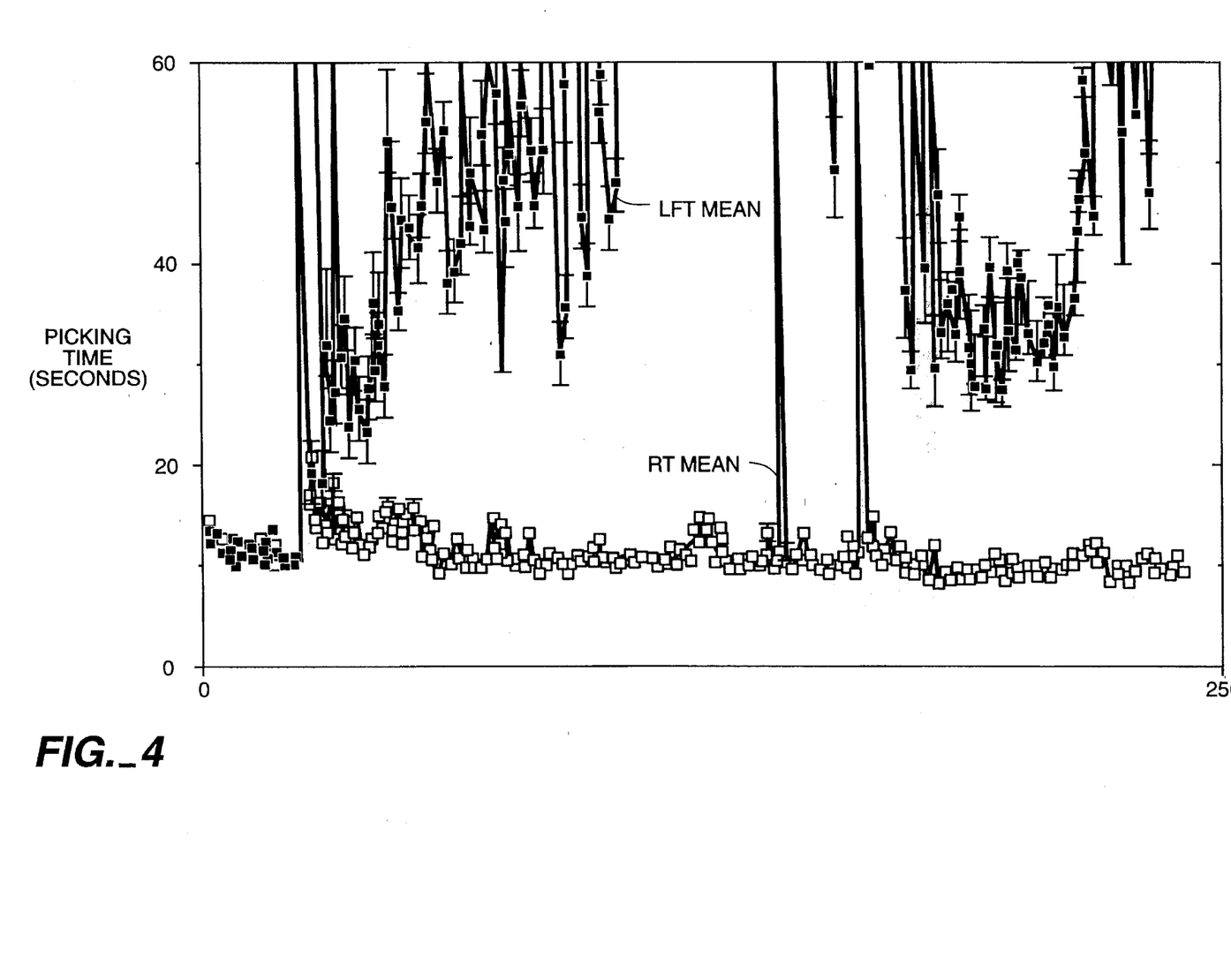
FIG. 4 shows the effect of a GABA-releasing implant placed in the subthalamic nucleus of a monkey with experimental parkinsonian movement disorder.

Improvement in the picking task performed by the left limb was observed after 14 days and persisted for more than 11 weeks (FIG. 4). After approximately eleven weeks, consistent with the depletion of GABA from the implanted rod, picking task performance again deteriorated over a period of two weeks. Following termination of the experiments, the animal was sacrificed, and the implant site studied histologically. The implant was found to be situated directly adjacent and lateral to the STN. The STN itself was not damaged, indicating the therapeutic effect was due to GABA release by the implant and not due to lesioning of the STN. The animal is sacrificed by means of a barbituric acid over-dose and its brain is prepared for histology. Histologic studies should reveal that the implants are positioned within the subthalamic nucleus, and that there is minimal tissue response to the implant.

EXAMPLE 3

Therapeutic, Focal Application Of GABA via Encapsulated Cell Implants for the Alleviation of Parkinsonian Symptoms NIT cells were shown to release up to 600 pg/cell/hr of GABA, NIT and RIN cell lines are pancreatic beta cell-derived cell lines. Pancreatic beta cells are known to contain GABA. These two cell lines were tested for basal release of GABA. Cells were tested for basal GABA release during static incubations in Hanks BSS. GABA released into the media was measured using HPLC. In one experiment, basal release of GABA from NIT cells was found to be approximately 12 fg/cell/min. In a similar experiment, RIN cells released 18 fg/cell/min.

GABA release was measured during static incubation experiments from encapsulated NIT cells in PAN/PVC fibers. Three fibers were hand-loaded with 10,000 to 20,000 NIT cells. The encapsulated cells were then incubated in growth media for two weeks prior to basal release studies. Over a 60 minute period, basal release was found to be approximately 60 pg/capsule/min.

Primates are trained in the behavioral picking task as described in Example 2. Responsiveness to Sinemet is determined prior to implantation after 6–8 weeks. Implantation is performed exactly as described in example 2 except a cellular encapsulation device is used in place of the polymeric implant.

NIT cells are grown according to Hamaquichi, K. et al., 1991 *Diabetes* 40:842. PAN/PVC encapsulation devices are prepared (0.5 cm length×600 μm i.d.), loaded with NIT cells and sealed at each end as described in U.S. Pat. No. 4,892,538 (Aebischer). GABA released from this loaded capsules is determined by derivitization of GABA with o-pthaldehyde/2-mercaptoethanol and detected electrochemically after elution from HPLC.

Implantation of encapsulated NIT cells leads to restoration of picking behavior similarly to Example 2.

EXAMPLE 4

Alleviation of Epileptogenic Symptoms In the GEPr Mouse

GEPr mice respond to sound and light stimuli with seizure activity. Baseline behavior levels are established for seizure onset in response to light or sound. The mice are then stereoticatically implanted with GABA releasing polymeric rods, made as described in Example 1. The rods are implanted in the inferior colliculus. The mice are then tested for alleviation of seizure activity in response to the stimuli.

What is claimed is:

1. A method for decreasing activity of at least one abnormally overactive output neuron in an abnormally active portion of a neural pathway in an individual having that condition, comprising implanting a static device adjacent at least one target neuron having neural activity, said target neuron being positioned presynaptically to said output neuron having abnormal over-activity, said target neuron receiving functional synaptic input, said static device focally releasing at least one compound which acts to inhibit neural activity in said target neuron, said inhibition decreasing said abnormal over-activity in said output neuron.

2. The method of claim 1 wherein said target neuron is in direct synaptic connection with said output neuron.

3. The method of claim 1 wherein said target neuron is in direct synaptic connection with an interneuron, said interneuron transmitting a neural signal to said output neuron.

4. The method of claim 1 wherein said decrease in activity effects an alleviation of movement disorders in said individual.

5. The method of claim 4 wherein said movement disorders comprise parkinsonian movement disorders.

6. The method of claim 5 wherein said compound is omega-conotoxin.

7. The method of claim 4 wherein said movement disorders comprise epileptiform seizure activity.

8. The method of claim 1 wherein said output neuron is located within the basal ganglia.

9. The method of claim 1 wherein said target neuron is located within the basal ganglia.

10. The method of claim 1 wherein said target neuron is located within the cerebral cortex.

11. The method of claim 1 wherein said output neuron is located within the cerebral cortex.

12. The method of claim 1 wherein said target neuron secretes glutamate.

13. The method of claim 1 wherein said target neuron contains at least one GABA receptor.

14. The method of claim 1 wherein said individual has Huntington's disease.

15. The method of claim 1 in which said one compound is secreted from living cells contained within at least one capsule having a semi-permeable wall.

16. The method of claim 1 in which said compound is secreted from GABA releasing cells.

17. The method of claim 1 in which said compound is secreted from NIT or RIN cells.

18. The method of claim 1 in which said compound is secreted from cell genetically engineered to release an inhibitory neuropeptide.

19. The method of claim 1 wherein said target neuron is located within the temporal lobe.

* * * * *